United States Patent
Oda et al.

(10) Patent No.: US 12,358,513 B2
(45) Date of Patent: Jul. 15, 2025

(54) MOTION SICKNESS REDUCTION SYSTEM AND INFORMATION PROCESSOR FOR MOTION SICKNESS REDUCTION

(71) Applicant: TOYOTA BOSHOKU KABUSHIKI KAISHA, Aichi (JP)

(72) Inventors: Daisuke Oda, Tokyo (JP); Akihiro Kanomune, Tokyo (JP)

(73) Assignee: TOYOTA BOSHOKU KABUSHIKI KAISHA, Aichi (JP)

( * ) Notice: Subject to any disclaimer, the term of this patent is extended or adjusted under 35 U.S.C. 154(b) by 231 days.

(21) Appl. No.: 17/967,161

(22) Filed: Oct. 17, 2022

(65) Prior Publication Data

US 2023/0131693 A1    Apr. 27, 2023

(30) Foreign Application Priority Data

Oct. 22, 2021    (JP) .................................. 2021-173352

(51) Int. Cl.
*B60W 40/08*    (2012.01)
*A61B 5/16*    (2006.01)

(52) U.S. Cl.
CPC ............ *B60W 40/08* (2013.01); *A61B 5/165* (2013.01); *B60W 2040/0872* (2013.01); *B60W 2540/221* (2020.02)

(58) Field of Classification Search
CPC ......... B60W 40/08; B60W 2040/0872; B60W 2540/221; A61B 5/165; A61B 5/0022; A61B 5/18
See application file for complete search history.

(56) References Cited

U.S. PATENT DOCUMENTS

| 2018/0313663 A1* | 11/2018 | Kobayashi | ............ B60W 50/14 |
| 2020/0353934 A1 | 11/2020 | Vulcu | |
| 2021/0402878 A1* | 12/2021 | Hwang | .................. B60K 35/00 |

FOREIGN PATENT DOCUMENTS

| JP | 2015-182755 | 10/2015 |
| JP | 2020-185378 | 11/2020 |
| WO | WO-2018138926 A1 * | 8/2018 |

OTHER PUBLICATIONS

Office Action issued in Corresponding JP Patent Application No. 2021-173352, dated Mar. 11, 2025, along with an English translation thereof.

(Continued)

*Primary Examiner* — Joseph H Feild
*Assistant Examiner* — Rufus C Point
(74) *Attorney, Agent, or Firm* — Greenblum & Bernstein, P.L.C.

(57) ABSTRACT

Provided is a motion sickness reduction system capable of providing a proper treatment tailored to a motion sickness state of each of two or more users. One aspect of the present disclosure is a motion sickness reduction system including a sensor that senses on-board states of the users aboard a vehicle, two or more communication terminals each assigned to the corresponding user, and an information processor that communicates with the communication terminals. The communication terminals each store motion sickness susceptibility data of the corresponding user to whom each communication terminal is assigned. The information processor performs a sickness level estimation process of estimating a sickness level of each user using the motion sickness susceptibility data and the corresponding on-board state sensed by the sensor, and a reduction treatment process of setting, for each user, a sickness reduction treatment based on the sickness level estimated.

5 Claims, 3 Drawing Sheets

(56) References Cited

OTHER PUBLICATIONS

Office Action issued in Corresponding CN Patent Application No. 202211283577.9, dated Apr. 10, 2025, along with an English translation thereof.

* cited by examiner

MOTION SICKNESS REDUCTION SYSTEM AND INFORMATION PROCESSOR FOR MOTION SICKNESS REDUCTION

CROSS-REFERENCE TO RELATED APPLICATIONS

This application claims the benefit of Japanese Patent Application No. 2021-173352 filed on Oct. 22, 2021 with the Japan Patent Office, the entire disclosure of which is incorporated herein by reference.

BACKGROUND

The present disclosure relates to a motion sickness reduction system and an information processor for motion sickness reduction.

A method of sensing states of occupants in a vehicle to reduce motion sickness is known (see Japanese Unexamined Patent Application Publication No. 2020-185378). In this method, the states of the occupants are perceived using the sensing data, and the vehicle is controlled in order to reduce the sickness.

SUMMARY

In the above-described method, the sickness state prediction is performed using the data of all of the occupants. Thus, there is room for improvement in the accuracy of perceiving the state of each of the occupants. In addition, since the same treatment is given to all of the occupants, a treatment according to the state of each occupant is not provided.

It is desirable that one aspect of the present disclosure provide a motion sickness reduction system capable of providing a proper treatment tailored to a motion sickness state of each of the users.

One aspect of the present disclosure is a motion sickness reduction system comprising: a sensor configured to sense, in a vehicle, on-board states of two or more users aboard the vehicle; two or more communication terminals each assigned to a corresponding one of the two or more users; and an information processor installed in the vehicle and configured to communicate with the two or more communication terminals.

The two or more communication terminals are each configured to store motion sickness susceptibility data of the corresponding one of the two or more users to whom each of the two or more communication terminals is assigned. The information processor is configured to perform: a sickness level estimation process of estimating, during travel of the vehicle, a sickness level of each of the two or more users using the motion sickness susceptibility data stored in a corresponding one of the two or more communication terminals and a corresponding one of the on-board states sensed by the sensor; and a reduction treatment process of setting a sickness reduction treatment based on the sickness level estimated, for each of the two or more users.

Such a configuration makes it possible to estimate the sickness level of each of the users aboard the vehicle based on the user's motion sickness susceptibility data stored in the corresponding communication terminal. Thus, a proper treatment tailored to a motion sickness state of each user can be provided.

In one aspect of the present disclosure, the information processor may be configured to, in the sickness level estimation process, transmit to the two or more communication terminals the on-board states of corresponding users, and to cause the two or more communication terminals to predict the sickness levels of the corresponding users using the motion sickness susceptibility data and the on-board states. Such a configuration allows for estimation of an individual sickness level without providing the user's personal information to the information processor. Thus, the personal information stored in the communication terminal can be protected.

One aspect of the present disclosure may further comprise a content provider configured to provide a general content to be shared by the two or more users in the vehicle. The information processor may be configured to switch provision of the general content to the two or more users by the content provider to provision of an individual content to each of the two or more users by a corresponding one of the two or more communication terminals, as the sickness reduction treatment. Such a configuration enables switching from a mode of providing a common content to the two or more users to a mode of providing an individual content in order to reduce the sickness. As a result, it is possible to satisfy both of a function of giving the two or more users experience in content sharing and a function of reducing motion sickness.

In one aspect of the present disclosure, the information processor may be configured to further perform a content determination process of determining the general content to be provided by the content provider based on a scheduled traveling route of the vehicle and on the motion sickness susceptibility data stored in each of the two or more communication terminals. Such a configuration enables selection of the general content on the basis of the road shapes of the scheduled traveling route, the motion sickness susceptibility of each user, and so on. Thus, the general content less likely to cause the users' motion sickness can be provided by the content provider.

In one aspect of the present disclosure, the information processor may be configured to cause a communication terminal corresponding to a user with a higher sickness level, among the two or more communication terminals, to perform attention calling to the user, as the sickness reduction treatment. Such a configuration enables facilitation of recovery of the user with a higher sickness level.

Another aspect of the present disclosure is an information processor for motion sickness reduction installed in a vehicle and configured to communicate with two or more communication terminals assigned to two or more users aboard the vehicle.

The information processor for motion sickness reduction is configured to perform: a sickness level estimation process of estimating, during travel of the vehicle, a sickness level of each of the two or more users using motion sickness susceptibility data of each of the two or more users stored in a corresponding one of the two or more communication terminals and an on-board state of each of the two or more users sensed in the vehicle; and a reduction treatment process of setting a sickness reduction treatment based on the sickness level estimated, for each of the two or more users.

Such a configuration enables provision of a proper treatment tailored to a motion sickness state of each of the two or more users.

BRIEF DESCRIPTION OF THE DRAWINGS

An example embodiment to which the present disclosure is applied will be described below with reference to the accompanying drawings, in which.

DETAILED DESCRIPTION OF EXEMPLARY EMBODIMENTS

1. First Embodiment

[1-1. Configuration]

Figure 1:
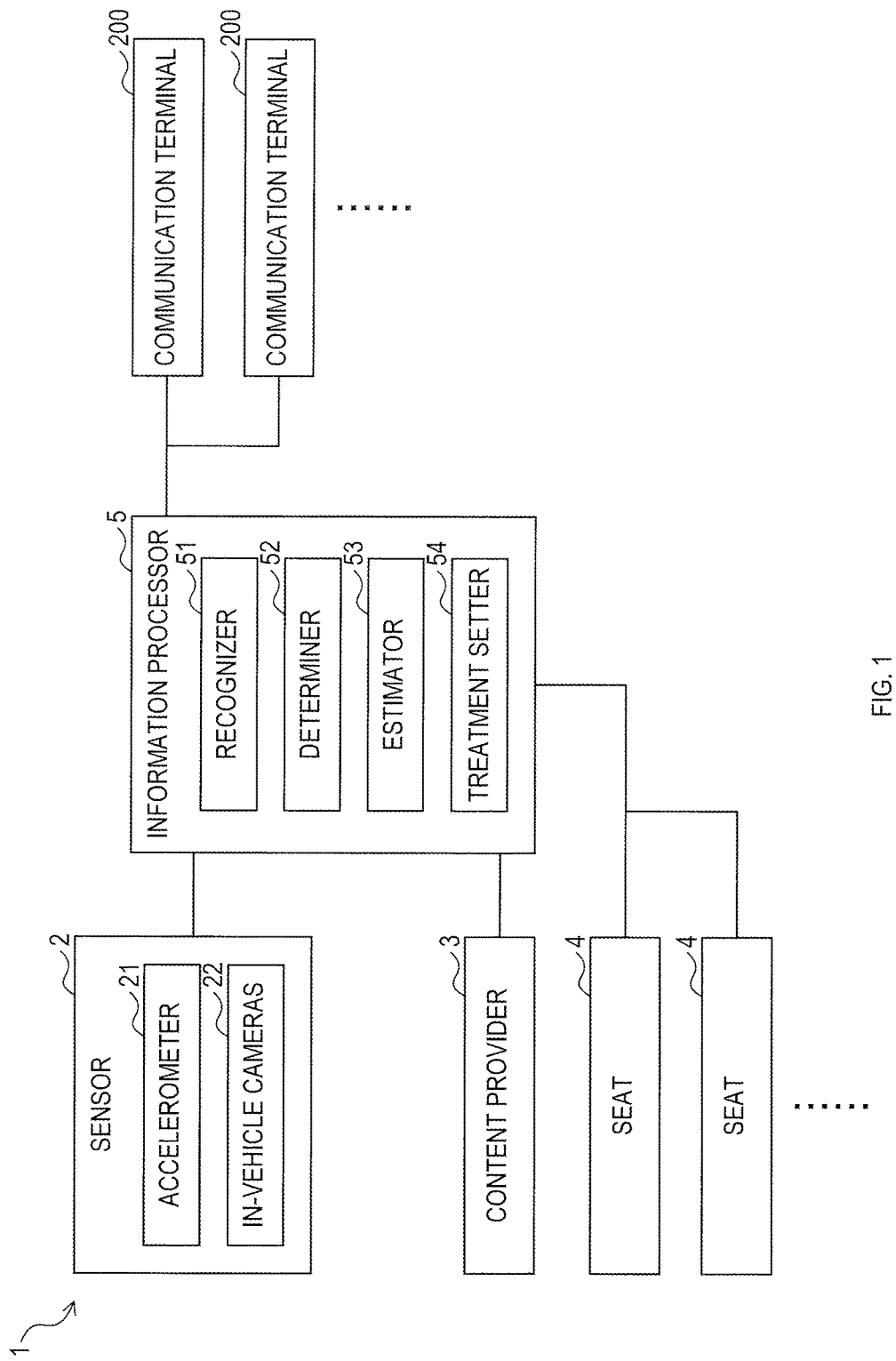
FIG. 1 is a schematic structural diagram illustrating a motion sickness reduction system according to the embodiment.
Figure 2:
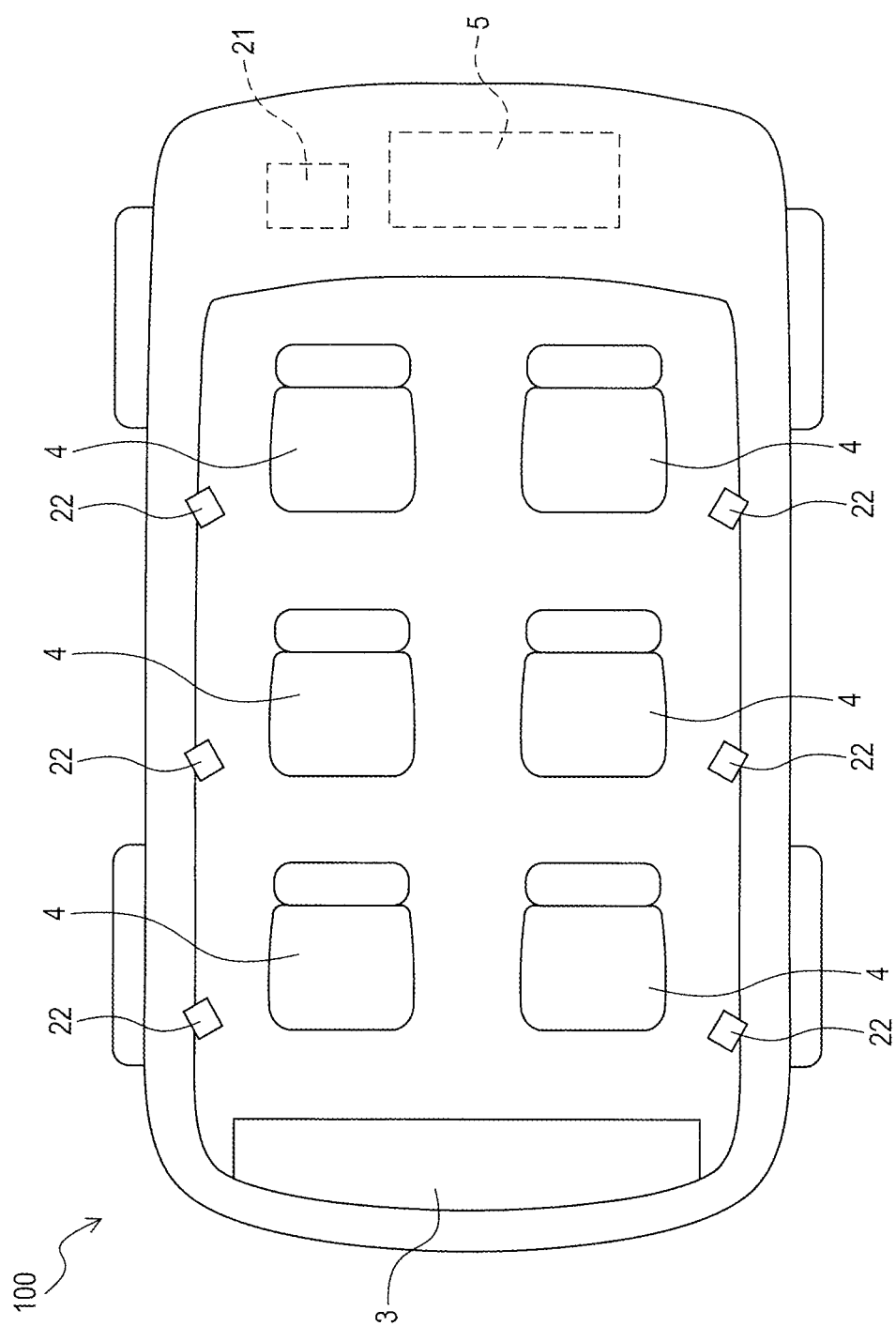
FIG. 2 is a schematic diagram of a vehicle to which the motion sickness reduction system in FIG. 1 is applied.

A motion sickness reduction system 1 shown in FIG. 1 is furnished in a vehicle 100 (see FIG. 2). The vehicle 100 in the present embodiment is a passenger car that can be boarded by two or more users carrying respective communication terminals 200 with them.

The motion sickness reduction system 1 comprises a sensor 2, a content provider 3, seats 4, an information processor 5, and the communication terminals 200.

<Sensor>

The sensor 2 is configured to sense, in the vehicle 100, on-board states of the users aboard the vehicle 100. The "on-board state" includes acceleration experienced by each user and a posture of each user.

The sensor 2 comprises an accelerometer 21 shown in FIG. 2, and in-vehicle cameras 22. The accelerometer 21 acquires the acceleration of the vehicle 100. The in-vehicle cameras 22 record the postures of the users seated in the seats 4.

<Content Provider>

The content provider 3 is configured to provide a general content to be shared by the users in the vehicle 100.

Examples of the content provider 3 used may include a large screen or display visible from all the seats 4 in the vehicle 100. The content provider 3 plays the general content (e.g., a moving image, such as a movie or a video) determined by the information processor 5.

<Seat>

The seats 4 are set up in a cabin space for the users in the vehicle 100. The users aboard the vehicle 100 are seated in any of the seats 4.

The seats 4 each comprise a mechanism for controlling, for example, postural change (e.g., reclining) or provision of airflow, and a sensor, such as a pressure sensor or a biological data sensor. The biological data sensor acquires, for example, a heart rate of each user.

<Information Processor>

The information processor 5 is installed in the vehicle 100, and is configured to communicate with the communication terminals 200.

As shown in FIG. 1, the information processor 5 comprises a recognizer 51, a determiner 52, an estimator 53, and a treatment setter 54.

The information processor 5 is configured with a computer comprising, for example, a processor, a storage medium such as a RAM/ROM, a communicator, and an input/output part. The information processor 5 may be incorporated in an electric control unit (ECU) of the vehicle 100. Part of the information processor 5 may be installed outside the vehicle 100 as a server (i.e., as ground equipment).

<Recognizer>

The recognizer 51 performs a recognition process of recognizing the communication terminals 200 carried by the users with them (i.e., assigned to the users) and of confirming that the users carrying such communication terminals 200 with them have boarded the vehicle 100.

Specifically, the recognizer 51 recognizes positions of the users (i.e., the occupied seats 4) based on position information received from the communication terminals 200, images taken by the in-vehicle cameras 22, and the data acquired by the sensors in the seats 4. Such recognition of the positions of the users is also performed at regular intervals during travel of the vehicle 100, in addition to the timing of boarding on the vehicle 100.

<Determiner>

The determiner 52 performs a content determination process of determining the general content to be provided by the content provider 3 from among playable contents, based on a scheduled traveling route of the vehicle 100 and on motion sickness susceptibility data stored in each of the communication terminals 200.

Here, the vehicle 100 may be an autonomously-driven vehicle running on the scheduled traveling route autonomously, or may be a manually-driven vehicle that a driver drives on the scheduled traveling route. In the case of the autonomously-driven vehicle, in which no driver is present, all the occupants are targets of sickness reduction, and thus, effects of the motion sickness reduction system 1 are more likely to be exerted.

Specifically, the determiner 52 predicts the magnitude of shakings during travel on the scheduled traveling route based on an acceleration history at the time of past travel on the scheduled traveling route stored in a database of the information processor 5.

The determiner 52 combines the predicted magnitude of shakings with data, such as the motion sickness susceptibility data of each user, the intensity of stimulus of each content, and each user's preference based on a past viewing history of the contents, thus calculating recommendation scores of the respective contents. The "intensity of stimulus of each content" is calculated based on, for example, an amount of change of a structural component (e.g., a motion vector) in each content, its brightness, and its category.

The determiner 52 determines, from among the playable contents, a content with the highest recommendation score calculated, as the general content, and commands the content provider 3 to play the general content.

<Estimator>

During travel of the vehicle 100, the estimator 53 performs a sickness level estimation process of estimating a sickness level of each user using the motion sickness susceptibility data stored in the corresponding communication terminal 200 and the on-board state sensed by the sensor 2.

The "motion sickness susceptibility data" include the user's age, gender, self-determined level of motion sickness susceptibility, and past motion sickness history. The "past motion sickness history" includes the on-board state (specifically, a vehicle acceleration and a head acceleration) at the time of occurrence of motion sickness in the past, and the sickness level that had been predicted at that time.

Specifically, in the sickness level estimation process, the estimator 53 first transmits, to the communication terminals 200, the on-board states of the corresponding users (i.e., the respective holders of the communication terminals 200). The on-board state of the user includes, for example, the vehicle acceleration and the head acceleration of the user, and the posture of the user.

The vehicle acceleration is acquired by the accelerometer 21. The head acceleration of the user is calculated based on the image taken by the in-vehicle camera 22. The estimator 53 uses, for estimation, an integrated value, for the past several minutes, of power spectra in the low-frequency region (e.g., 0.2 Hz or more and 1 Hz or less) of each of these accelerations.

The posture of the user is calculated based on the image taken by the in-vehicle cameras 22. The estimator 53 uses, for estimation, a categorical variable representing the direction of the user's face (i.e., how much the user's head is bent down) in several levels.

Next, the estimator 53 causes the communication terminals 200 to each predict the sickness level of the corresponding user using the motion sickness susceptibility data stored in each communication terminal 200 and the on-board state transmitted to the communication terminal 200.

In other words, the estimator 53 transmits, to each communication terminal 200, a command to perform calculation with the motion sickness susceptibility data and the on-board state serving as input, and with the sickness level serving as output. The estimator 53 acquires the sickness levels predicted by the communication terminals 200 as estimation results of the sickness levels of the corresponding users.

<Treatment Setter>

The treatment setter 54 performs a reduction treatment process of setting, for each of the users, a sickness reduction treatment based on the sickness level estimated in the sickness level estimation process.

Specifically, the treatment setter 54 switches, as the sickness reduction treatment, provision of the general content to the users by the content provider 3, to provision of individual contents to the respective users by the corresponding communication terminals 200.

In other words, when the sickness levels of some of the users are higher than or equal to a threshold set in advance, the treatment setter 54 commands the content provider 3 to stop playing the general content. Further, the treatment setter 54 commands the communication terminals 200 to each play the individual content.

In addition, as the sickness reduction treatment, the treatment setter 54 causes the communication terminal 200 corresponding to the user with a higher sickness level (i.e., the communication terminal 200 carried by the user whose sickness level is higher than or equal to the threshold), among the communication terminals 200, to perform attention calling to the user.

Examples of the attention calling to the user may include an indication to encourage the user to stop watching the content and take a rest. The attention calling may be performed together with playback of the individual content. For example, the communication terminal 200 may perform a guiding control as the attention calling to the user. Examples of the guiding control may include a control to indicate suggestion, to the user, of a direction less likely to induce sickness (e.g., an upper direction), and a control to stop the individual content when the user faces in a direction more likely to induce sickness (i.e., a lower direction).

The direction more likely to induce the user's sickness is determined by the treatment setter 54 or by the communication terminal 200 based on the orientation of the communication terminal 200 detected by a gyroscope sensor of the communication terminal 200 and on the traveling direction of the vehicle 100 detected by the accelerometer of the communication terminal 200. In addition, the control for attention calling may be performed using the user's posture acquired by the in-vehicle camera 22.

The treatment setter 54 also causes, as the sickness reduction treatment, the seat 4 occupied by the user with, a higher sickness level, among the seats 4, to perform a sickness reduction control. Examples of the sickness reduction control may include a rearward reclining of a seatback and provision of airflow to the user.

The treatment setter 54 performs no particular treatment, such as the above-described attention calling or the sickness reduction control, to the user with a lower sickness level (i.e., the user whose sickness level is lower than the threshold).

<Communication Terminal>

The communication terminal 200 is a portable computer comprising, for example, a processor, a storage medium such as a RAM/ROM, a communicator, and an input/output part.

Examples of the communication terminal 200 may include a smartphone, a tablet computer, and a notebook computer. Transmission and reception of the data between the communication terminal 200 and the information processor 5 are performed through wireless communication. Examples of the wireless communication available may include short-range wireless communication and wireless LAN.

The communication terminal 200 has a program (i.e., an application) installed thereon for using the motion sickness reduction system 1. This program includes a determination formula for predicting the sickness level (i.e., a prediction model). The communication terminal 200 uses the determination formula to perform prediction of the sickness level based on a command from the information processor 5.

The determination formula for predicting the sickness level is formulated in advance by a statistical method. In the statistical method, the on-board state of the user and the prediction result of the past sickness level of the user serve as explanatory variables (i.e., independent variables), and the current sickness level of the user serves as a response variable. The "on-board state of the user" used as the explanatory variable in the determination formula includes the vehicle acceleration and the head acceleration of the user, and the posture of the user, as described above.

Examples of the statistical method used may include multivariate analysis, supervised machine learning, and a combination thereof. The supervised machine learning is performed using the sickness levels of the users as teacher data, and using the above-described explanatory variables as input data.

In a learning step, multiple combinations of labeled explanatory variables (i.e., of the teacher data) are analyzed by a machine learning circuit. The machine learning circuit learns, from the multiple labeled data, feature amounts for classifying the combinations of the explanatory variables into two or more labels (i.e., the sickness levels), thus establishing the determination formula. The communication terminal 200 may be configured to receive the updated determination formula as appropriate from a not-shown server.

The communication terminal 200 stores the motion sickness susceptibility data of the user to whom it is assigned (i.e., of the holder of the communication terminal 200). The motion sickness susceptibility data is input by the user when user registration of the motion sickness reduction system 1 is made via the communication terminal 200 in which the application is installed.

[1-2. Process]

Figure 3:
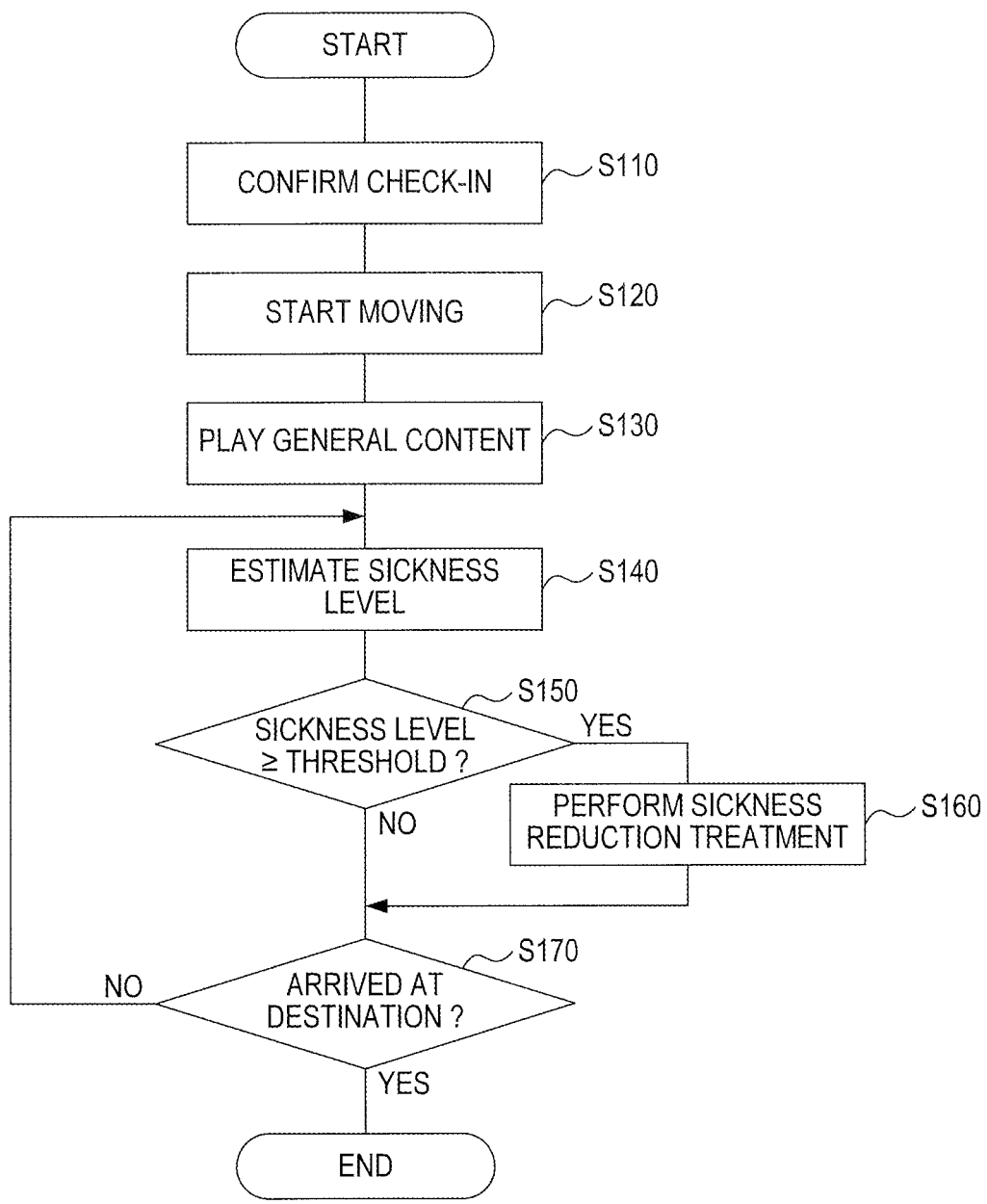
FIG. 3 is a flow diagram schematically illustrating a process performed by an information processor shown in FIG. 1.

One example of the process performed by the information processor 5 will be described below with reference to the flow diagram in FIG. 3.

In this process, the information processor 5 first performs a check-in confirmation to confirm that the users have boarded the vehicle 100 (step S110). The check-in confirmation is performed by recognizing the communication terminals 200 carried by the users who have made boarding registrations (i.e., reservations) in advance.

After performing the check-in confirmation, the information processor 5 causes the vehicle 100 to start moving (step S120). In the case where the vehicle 100 is autonomously driven, the information processor 5 starts a driving control program. In the case where the vehicle 100 is manually driven, the information processor 5 issues a command for a driver to start driving.

The information processor 5 determines the general content to be provided by the content provider 3, and causes the content provider 3 to play the general content (step S130). After start of playback of the general content, the information processor 5 estimates the sickness level of each user in cooperation with the communication terminal 200 of the user (step S140).

After estimating the sickness level, the information processor 5 determines whether the sickness level of each user is higher than or equal to the threshold (step S150). If the sickness level of at least one user is higher than or equal to the threshold (S150: YES), the information processor 5 performs the sickness reduction treatment according to the sickness level of the user (step S160). In contrast, if there is no user whose sickness level is higher than or equal to the threshold (S150: NO), the information processor 5 does not perform the sickness reduction treatment.

After determining whether to perform the sickness reduction treatment (and after performing the sickness reduction treatment in some instances), the information processor 5 determines whether the vehicle 100 has arrived at a destination (step S170). If the vehicle 100 has arrived at the destination (S170: YES), the information processor 5 terminates the process. In contrast, if the vehicle 100 has not arrived at the destination yet (S170: NO), the information processor 5 repeats the steps starting from the sickness level estimation (S140).

[1-3. Effects]

The above-detailed embodiment produces the following effects.

(1a) The sickness level of each of the users aboard the vehicle 100 can be estimated based on the user's motion sickness susceptibility data stored in the corresponding communication terminal 200. Thus, a proper treatment tailored to a motion sickness state of each user can be provided.

(1b) Prediction of the sickness level using the motion sickness susceptibility data is performed in the communication terminal 200, thus allowing for estimation of an individual sickness level without providing the user's personal information to the information processor 5. Thus, the personal information stored in the communication terminal 200 can be protected.

(1c) As the sickness reduction treatment, provision of the general content is switched to provision of the individual content for each user, thus enabling switching from a mode of providing a common content to the two or more users to a mode of providing an individual content in order to reduce the sickness. As a result, it is possible to satisfy both of a function of giving the two or more users experience in content sharing and a function of reducing motion sickness.

(1d) The general content is determined based on the scheduled traveling route of the vehicle 100 and on the motion sickness susceptibility data, thus enabling selection of the general content on the basis of the road shapes of the scheduled traveling route, the motion sickness susceptibility of each user, and so on. Thus, the general content less likely to cause the users' motion sickness can be provided by the content provider 3.

(1e) As the sickness reduction treatment, the communication terminal 200 performs attention calling to the user. This enables facilitation of recovery of the user with a higher sickness level.

2. Other Embodiments

The embodiment of the present disclosure has been described so far; however, the present disclosure can be practiced in various forms without being limited to the above-described embodiment.

(2a) In the motion sickness reduction system of the above-described embodiment, prediction of the sickness level does not necessarily have to be performed in the communication terminal. For example, a configuration may be employed in which the information processor receives the motion sickness susceptibility data from the communication terminals and estimates the sickness level using the determination formula.

(2b) In the motion sickness reduction system of the above-described embodiment, determination, by the information processor, of the general content to be provided by the content provider does not necessarily have to be performed based on the scheduled traveling route of the vehicle and on the motion sickness susceptibility data.

Moreover, the motion sickness reduction system of the above-described embodiment does not necessarily have to comprise the content provider. In other words, the motion sickness reduction system may be configured to provide the contents using the individual communication terminals alone.

(2c) The motion sickness reduction system of the above-described embodiment may also be applied to vehicles other than passenger cars, such as railroad vehicles, ships, and aircrafts.

(2d) The function of a single element in the above-described embodiments may be performed separately by two or more elements, and the function performed by two or more elements may be performed inclusively by a single element. Part of the configuration in the above-described embodiments may be omitted. At least part of the configuration in the above-described embodiments may be added to or replace another configuration in the above-described embodiments. Any and all modes encompassed by the technical idea defined by the language of the claims are embodiments of the present disclosure.

What is claimed is:

1. A motion sickness reduction system, comprising:
a sensor configured to sense, in a vehicle, on-board states of two or more users aboard the vehicle;
two or more communication terminals each assigned to a corresponding one of the two or more users; and
an information processor installed in the vehicle and configured to communicate with the two or more communication terminals,
the two or more communication terminals each being configured to store motion sickness susceptibility data of the corresponding one of the two or more users to whom each of the two or more communication terminals is assigned, the information processor being configured to perform:
- a sickness level estimation process of estimating, during travel of the vehicle, a sickness level of each of the two or more users using the motion sickness susceptibility data stored in a corresponding one of the two or more communication terminals and a corresponding one of the on-board states sensed by the sensor; and
- a reduction treatment process of setting a sickness reduction treatment based on the sickness level estimated, for each of the two or more users, wherein the information processor is configured to, in the sickness level estimation process, transmit to the two or more communication terminals the on-board states of corresponding users, and to cause the two or more communication terminals to predict the sickness levels of the corresponding users using the motion sickness susceptibility data and the on-board states.

2. The motion sickness reduction system according to claim 1, wherein the information processor is configured to cause a communication terminal corresponding to a user with a higher sickness level, among the two or more communication terminals, to perform attention calling to the user, as the sickness reduction treatment.

3. A motion sickness reduction system, comprising:
- a sensor configured to sense, in a vehicle, on-board states of two or more users aboard the vehicle;
- two or more communication terminals each assigned to a corresponding one of the two or more users;
- an information processor installed in the vehicle and configured to communicate with the two or more communication terminals; and
- a content provider configured to provide a general content to be shared by the two or more users in the vehicle, the two or more communication terminals each being configured to store motion sickness susceptibility data of the corresponding one of the two or more users to whom each of the two or more communication terminals is assigned, the information processor being configured to perform:
- a sickness level estimation process of estimating, during travel of the vehicle, a sickness level of each of the two or more users using the motion sickness susceptibility data stored in a corresponding one of the two or more communication terminals and a corresponding one of the on-board states sensed by the sensor; and
- a reduction treatment process of setting a sickness reduction treatment based on the sickness level estimated, for each of the two or more users, and wherein the information processor is configured to switch provision of the general content to the two or more users by the content provider to provision of an individual content to each of the two or more users by a corresponding one of the two or more communication terminals, as the sickness reduction treatment.

4. The motion sickness reduction system according to claim 3, wherein the information processor is configured to further perform a content determination process of determining the general content to be provided by the content provider based on a scheduled traveling route of the vehicle and on the motion sickness susceptibility data stored in each of the two or more communication terminals.

5. An information processor for motion sickness reduction installed in a vehicle and configured to communicate with two or more communication terminals assigned to two or more users aboard the vehicle, the information processor being configured to perform:
- a sickness level estimation process of estimating, during travel of the vehicle, a sickness level of each of the two or more users using motion sickness susceptibility data of each of the two or more users stored in a corresponding one of the two or more communication terminals and an on-board state of each of the two or more users sensed in the vehicle; and
- a reduction treatment process of setting a sickness reduction treatment based on the sickness level estimated, for each of the two or more users, wherein the information processor is further configured to, in the sickness level estimation process, transmit to the two or more communication terminals the on-board states of corresponding users, and to cause the two or more communication terminals to predict the sickness levels of the corresponding users using the motion sickness susceptibility data and the on-board states.

* * * * *